United States Patent
Jasserand et al.

(10) Patent No.: US 6,770,649 B2
(45) Date of Patent: Aug. 3, 2004

(54) 1-[1-(HETERO)ARYL-1-PERHYDROXYALKYLMETHYL]-PIPERAZINE COMPOUNDS, PROCESS FOR THEIR PREPARATION AND PHARMACEUTICAL COMPOSITIONS CONTAINING THEM

(75) Inventors: Daniel Jasserand, Hannover (DE); Ulf Preuschoff, Lehrte/Ahlten (DE); Jochen Antel, Bad Muender (DE); Samuel David, Hannover (DE); Holger Sann, Hannover (DE); Reinhard Brueckner, Hannover (DE); Dania Reiche, Adelheidsdorf (DE); Christian Eeckhout, Lindwedel (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 6 days.

(21) Appl. No.: 10/242,678

(22) Filed: Sep. 13, 2002

(65) Prior Publication Data

US 2003/0125557 A1 Jul. 3, 2003

(30) Foreign Application Priority Data

Sep. 13, 2001 (DE) .......................... 101 45 044

(51) Int. Cl.$^7$ .................... C07D 333/20; C07D 307/52; C07D 407/06; A61K 31/381; A61P 1/00
(52) U.S. Cl. ......................... 514/252.12; 514/252.13; 514/254.11; 514/255.04; 544/374; 544/379; 544/400
(58) Field of Search ........................ 514/252.12, 252.13, 514/254.11, 255.04; 544/374, 379, 400

(56) References Cited

FOREIGN PATENT DOCUMENTS

| EP | 0428434 | 5/1991 |
|----|---------|--------|
| EP | 0474561 | 3/1992 |
| EP | 0709375 | 5/1996 |
| WO | WO 01/77069 | * 10/2001 |

* cited by examiner

*Primary Examiner*—Bruck Kifke
(74) *Attorney, Agent, or Firm*—Crowell & Moring LLP

(57) ABSTRACT

Novel 1-[1-(hetero)aryl-1-perhydroxyalkylmethyl]-piperazine compounds which are antagonistic to tachykinin receptors, of the general formula I,

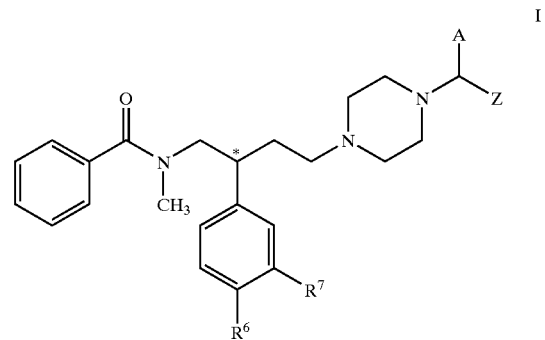

wherein $R^6$, $R^7$, A and Z have the meanings given in the description, and pharmaceutical compositions containing these compounds, as well as a process for the preparation of such compounds and intermediate products of this process.

12 Claims, No Drawings

1-[1-(HETERO)ARYL-1-PERHYDROXYALKYLMETHYL]-PIPERAZINE COMPOUNDS, PROCESS FOR THEIR PREPARATION AND PHARMACEUTICAL COMPOSITIONS CONTAINING THEM

BACKGROUND OF THE INVENTION

The present invention relates to novel 1-[1-(hetero)aryl-1-perhydroxyalkylmethyl]-piperazine compounds which are tachykinin receptor antagonists and to medicaments containing these compounds. Furthermore, the invention relates to a process for preparing the novel piperazine compounds and intermediate products of this process.

The tachykinins include the naturally-occurring neuropeptides substance P, neurokinin A and neurokinin B. The tachykinins act as agonists of receptors occurring in larger mammals and humans, such as the neurokinin (=NK)-1 receptor, the NK-2 receptor and the NK-3 receptor. Artificially prepared compounds which are tachykinin receptor antagonists are usually classified according to their relative ability to bind to one or more of the aforementioned three receptor subtypes. In the physiological process the tachykinins play e.g. an important part in the transmission of pain, emesis, neurogenic inflammations, bladder inflammation, inflammatory joint diseases or asthmatic complaints.

Inter alia, piperazine derivatives which act as antagonists to the NK-2 receptor are already known from published European Patent application no. EP 474,561.

Further piperazine derivatives which can act as antagonists to tachykinin receptors are known from published PCT Patent application no. WO 96/10568.

SUMMARY OF THE INVENTION

It was an object of the present invention to provide novel active substances having properties antagonistic to tachykinin receptors and an improved activity profile.

Another object of the invention is to provide new active compounds which are suitable for treating peripheral disorders.

A particular of object of the invention was to provide active compounds which are useful to treat functional and inflammatory disorders of the gastrointestinal tract.

These and other objects are achieved in accordance with the present invention by providing a compound corresponding to the formula I:

wherein
A is naphthyl, phenyl optionally substituted by hydroxy, mono- or bicyclic heteroaryl or $C_{3-6}$-alkenyl optionally substituted by phenyl, Z is a subgroup corresponding to the formula $$\begin{array}{c} -(CHOR^1)_k \\ (CHOR^2)_l \\ (CHOR^3)_m \\ (CHOR^4)_n \\ CH_2OR^5 \end{array}$$

wherein
$R^1$ is hydrogen or lower alkanoyl, or together with another substituent, selected from the group consisting of $R^2$, $R^3$, $R^4$ and $R^5$, may form a 5- or 6-member ring bridged by carbonyl, thiocarbonyl or by methylene optionally substituted by lower alkyl or $C_{4-5}$-alkylene, $R^2$ is hydrogen or lower alkanoyl, or together with another substituent, selected from the group consisting of $R^1$, $R^3$, $R^4$ and $R^5$, may form a 5- or 6-member ring bridged by carbonyl, thiocarbonyl or by methylene optionally substituted by lower alkyl or $C_{4-5}$-alkylene, $R^3$ is hydrogen or lower alkanoyl, or together with another substituent, selected from the group consisting of $R^1$, $R^2$, $R^4$ and $R^5$, may form a 5- or 6-member ring bridged by carbonyl, thiocarbonyl or by methylene optionally substituted by lower alkyl or $C_{4-5}$-alkylene, $R^4$ is hydrogen or lower alkanoyl, or together with another substituent, selected from the group consisting of $R^1$, $R^2$, $R^3$ and $R^5$, may form a 5- or 6-member ring bridged by carbonyl, thiocarbonyl or by methylene optionally substituted by lower alkyl or $C_{4-5}$-alkylene, $R^5$ is hydrogen or lower alkanoyl, or together with another substituent, selected from the group consisting of $R^1$, $R^2$, $R^3$ and $R^4$, may form a 5- or 6-member ring bridged by carbonyl, thiocarbonyl or by methylene optionally substituted by lower alkyl or $C_{4-5}$-alkylene, k is 0 or 1,
l is 0 or 1,
m is 0 or 1 and
n is 0 or 1,
$R^6$ is halogen or hydrogen, and
$R^7$ is halogen or hydrogen, or a physiologically compatible acid addition salt thereof.

In accordance with a further aspect of the invention, the objects are achieved by providing a method of inhibiting a functional or inflammatory disorder of a lower intestinal tract of a mammal which involves increased sensitivity to pain or impaired stool passage in the colon region, said method comprising administering to said mammal a pharmaceutically effective amount of a piperazine compound as described above.

In yet another aspect of the invention, the objects are achieved by providing a process for the preparation of a compound corresponding to formula I:

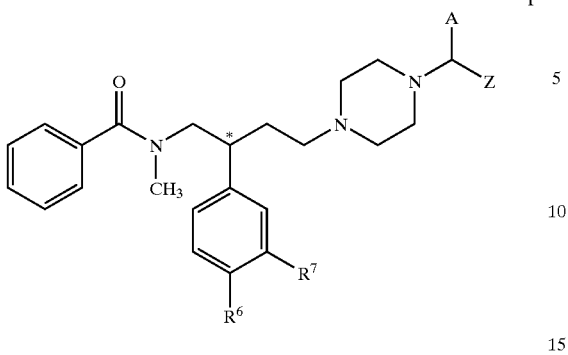

wherein
A is naphthyl, phenyl optionally substituted by hydroxy, mono- or bicyclic heteroaryl or $C_{3-6}$-alkenyl optionally substituted by phenyl, Z is a subgroup corresponding to the formula

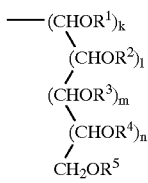

wherein
R$^1$ is hydrogen or lower alkanoyl, or together with another substituent, selected from the group consisting of R$^2$, R$^3$, R$^4$ and R$^5$, may form a 5- or 6-member ring bridged by carbonyl, thiocarbonyl or by methylene optionally substituted by lower alkyl or $C_{4-5}$-alkylene, R$^2$ is hydrogen or lower alkanoyl, or together with another substituent, selected from the group consisting of R$^1$, R$^3$, R$^4$ and R$^5$, may form a 5- or 6-member ring bridged by carbonyl, thiocarbonyl or by methylene optionally substituted by lower alkyl or $C_{4-5}$-alkylene, R$^3$ is hydrogen or lower alkanoyl, or together with another substituent, selected from the group consisting of R$^1$, R$^2$, R$^4$ and R$^5$, may form a 5- or 6-member ring bridged by carbonyl, thiocarbonyl or by methylene optionally substituted by lower alkyl or $C_{4-5}$-alkylene, R$^4$ is hydrogen or lower alkanoyl, or together with another substituent, selected from the group consisting of R$^1$, R$^2$, R$^3$ and R$^5$, may form a 5- or 6-member ring bridged by carbonyl, thiocarbonyl or by methylene optionally substituted by lower alkyl or $C_4$-alkylene, R$^5$ is hydrogen or lower alkanoyl, or together with another substituent, selected from the group consisting of R$^1$, R$^2$, R$^3$ and R$^4$, may form a 5- or 6-member ring bridged by carbonyl, thiocarbonyl or by methylene optionally substituted by lower alkyl or $C_{4-5}$-alkylene, k is 0 or 1,
l is 0 or 1,
m is 0 or 1 and
n is 0 or 1,
R$^6$ is halogen or hydrogen, and
R$^7$ is halogen or hydrogen, or a physiologically compatible acid addition salt thereof, said process comprising reacting a compound of formula II:

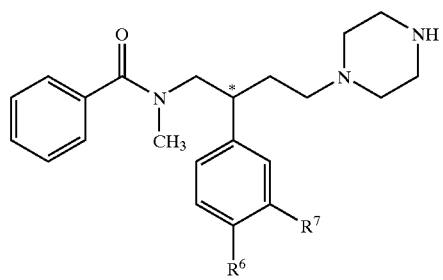

wherein R$^6$ and R$^7$ have the above meanings, with a compound of formula III:

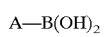

A—B(OH)$_2$   III wherein A has the above meaning, and with a compound of formula IV:

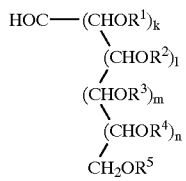

wherein R$^1$, R$^2$, R$^3$, R$^4$, R$^5$, k, l, m und n have the above meanings, and optionally acylating a resulting compound of Formula I, wherein at least one substituent selected from R$^1$, R$^2$, R$^3$, R$^4$ and R$^5$ is hydrogen, in the subgroup Z by reacting with a compound corresponding to formula VIII:

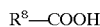

R$^8$—COOH   (VIII)

wherein R$^8$ is a straight-chain or branched alkyl with 1 to 3 carbon atoms, or optionally carbonylating or thiocarbonylating a resulting compound of Formula I, wherein at least two substituents selected from R$^1$, R$^2$, R$^3$, R$^4$ and R$^5$ are hydrogen, in the subgroup Z by reacting the compound of formula I with a reactive carbonyl- or thiocarbonyl synthesis equivalent, or optionally converting a resulting compound of Formula I, wherein at least two substituents, selected from R$^1$, R$^2$, R$^3$, R$^4$ and R$^5$ are hydrogen, to a 5- or 6-member ring derivative bridged by methylene and optionally substituted by lower alkyl or $C_{4-5}$-alkylene by reacting the compound of Formula I in the subgroup Z with a di-lower alkylketone or a $C_{5-6}$-cycloalkylketone, and optionally converting compound of Formula I into a corresponding acid addition salt, or optionally converting an acid addition salt into a free compound of Formula I.

A still further aspect of the invention involves the provision of a compound compound corresponding to formula II:

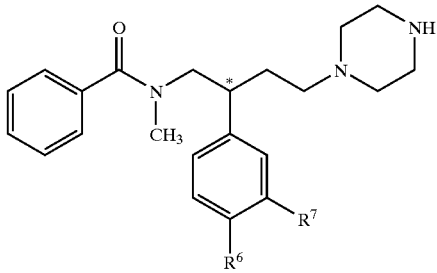

wherein $R^6$ is halogen or hydrogen, and $R^7$ is halogen or hydrogen.

DETAILED DESCRIPTION OF PREFERRED EMBODIMENTS

It has now been found, surprisingly, that a group of novel 1-[1-(hetero)aryl-1-perhydroxyalkylmethyl]-piperazine compounds is distinguished by properties antagonistic to tachykinin receptors, in particular to NK-2 receptors, and has a marked action component directed at the peripheral region. Accordingly, the group of compounds according to the invention appears particularly suitable for the treatment of peripheral disorders in which tachykinins, in particular neurokinin A, participate as transfer agents, for example for the treatment and/or prophylaxis of functional and inflammatory disorders of the gastrointestinal tract. The designation (hetero)aryl is to be understood within the scope of the present invention as possibly comprising both aryl and heteroaryl radicals.

The invention thus relates to novel 1-[1-(hetero)aryl-1-perhydroxyalkylmethyl]-piperazine compounds of the general formula I,

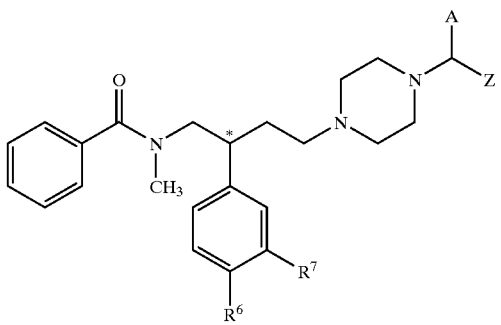

wherein

A is naphthyl, phenyl optionally substituted by hydroxy, mono- or bicyclic heteroaryl or $C_{3-6}$-alkenyl optionally substituted by phenyl, Z stands for a subgroup of the general formula

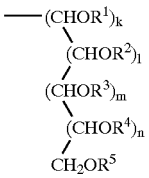

wherein $R^1$ is hydrogen or lower alkanoyl, or together with another substituent, selected from the group consisting of $R^2$, $R^3$, $R^4$ and $R^5$, may form a 5- or 6-member ring bridged by carbonyl, thiocarbonyl or by methylene optionally substituted by lower alkyl or $C_{4-5}$-alkylene, $R^2$ is hydrogen or lower alkanoyl, or together with another substituent, selected from the group consisting of $R^1$, $R^3$, $R^4$ and $R^5$, may form a 5- or 6-member ring bridged by carbonyl, thiocarbonyl or by methylene optionally substituted by lower alkyl or $C_{4-5}$-alkylene, $R^3$ is hydrogen or lower alkanoyl, or together with another substituent, selected from the group consisting of $R^1$, $R^2$, $R^4$ and $R^5$, may form a 5- or 6-member ring bridged by carbonyl, thiocarbonyl or by methylene optionally substituted by lower alkyl or $C_{4-5}$-alkylene, $R^4$ is hydrogen or lower alkanoyl, or together with another substituent, selected from the group consisting of $R^1$, $R^2$, $R^3$ and $R^5$, may form a 5- or 6-member ring bridged by carbonyl, thiocarbonyl or by methylene optionally substituted by lower alkyl or $C_{4-5}$-alkylene, $R^5$ is hydrogen or lower alkanoyl, or together with another substituent, selected from the group consisting of $R^1$, $R^2$, $R^3$ and $R^4$, may form a 5- or 6-member ring bridged by carbonyl, thiocarbonyl or by methylene optionally substituted by lower alkyl or $C_{4-5}$-alkylene, k is 0 or 1, l is 0 or 1, m is 0 or 1, n is 0 or 1, $R^6$ is halogen or hydrogen, and $R^7$ is halogen or hydrogen, and physiologically compatible acid addition salts of compounds of Formula I. Furthermore, the invention also includes pharmaceutical compositions containing the compounds of Formula I. Additionally, the invention relates to a process for the preparation of compounds of Formula I and intermediate products of this process.

Whenever in the compounds of Formula I or in other compounds described within the scope of the present invention substituents are or contain lower alkyl, these may each be straight-chain or branched and possess 1 to 4 carbon atoms. Whenever substituents in compounds of Formula I are halogen, fluorine, chlorine or bromine are suitable. Chlorine is preferred. Where substituents contain lower alkanoyl, this may be straight-chain or branched and possess 2 to 4 carbon atoms. Acetyl is the preferred lower alkanoyl.

The subgroup A preferably stands for monocyclic heteroaryl. Suitable monocyclic heteroaryls are in particular thiophene, furan and pyrrole. Thiophene and furan are preferred. Where A stands for bicyclic heteroaryl, in particular benzothiophene, benzofuran and indole are suitable. Where A stands for $C_{3-6}$-alkenyl optionally substituted by phenyl, the alkenyl chain may be straight-chain or branched and stands in particular for 1-alkenyl.

Where a substituent covered by the subgroup Z from the group consisting of $R^1$, $R^2$, $R^3$, $R^4$ and $R^5$ together with another substituent selected from this group stands for a 5- or 6-member ring bridged by methylene optionally substituted by lower alkyl or $C_{4-5}$-alkylene, in particular 5- or 6-member rings bridged by methylene, 1,1-dimethylmethylene, 1,1-spiro-tetramethylene-methylene or 1,1-spiro-pentamethylene-methylene are suitable. Corresponding 5- or 6-member rings bridged by carbonyl are to be regarded as cyclic carbonates. Corresponding 5- or 6-member rings bridged by thiocarbonyl are to be regarded as cyclic thiocarbonates. k preferably stands for 1. n preferably stands for 0. Z thus preferably represents an optionally substituted 1,2-diol radical, a 1,2,3-triol radical or a 1,2,3,4-tetrol radical. The carbon atoms bearing the substituents $R^1$, $R^2$, $R^3$ and $R^4$ are asymmetric and may each occur in two different configurations. Due to this, Z may occur in several stereoisomeric forms. The present invention also covers, in addition to the compounds of Formula I which contain mixtures of stereoisomeric forms of the subgroup Z, compounds of Formula I in which isomerically pure subgroups Z are contained. Preferred subgroups Z are xylo-1,2,3,4-tetrahydroxybutyl, lyxo-1,2,3,4-tetrahydroxybutyl, arabino-1,2,3,4-tetrahydroxybutyl, threo-1,2,3-trihydroxypropyl, erythro-1,2,3-trihydroxypropyl and glycero-1,2-dihydroxyethyl. The carbohydrates selected from the D-series of the carbohydrates on which the subgroups Z are based mostly produce the most beneficial results. Diastereomerically pure subgroups Z are preferred.

Particularly preferred compounds of Formula I are selected from the group consisting of N-((2S)-2-(3,4-dichlorophenyl)-4-{4-[(2S,3R,4R)-2,3,4,5-tetrahydroxy-1-(3-thienyl)pentyl]-1-piperazinyl}butyl)-N-methylbenzamide;

N-((2S)-2-(3,4-dichlorophenyl)-4-{4[(2S)-2,3-dihydroxy-1-(2-furyl)propyl]-1-piperazinyl}-butyl)-N-methylbenzamide; (2S)-2-(acetyloxy)-3-{4-[(3S)-4-[benzoyl(methyl)amino]-3-(3,4-dichlorophenyl)butyl]-1-piperazinyl}-3-(2-furyl)propylacetate;

N-[(2S)-2-(3,4)-dichlorophenyl)-4-(4-{2-furyl[(4S)-2-oxo-1,3-dioxolan-4-yl]methyl}-1-piperazinyl)butyl]-N-methylbenzamide;

N-((2S)-2-(3,4-dichlorophenyl)-4-{4[(1S,2R)-2,3-dihydroxy-1-(3-thienyl)propyl]-1-piperazinyl}-butyl)-N-methylbenzamide;

N-((2S)-2-(3,4-dichlorophenyl)-4-{4[(2S)-2,3-dihydroxy-1-(3-furyl)propyl]-1-piperazinyl}-butyl)-N-methylbenzamide;

N-((2S)-2-(3,4-dichlorophenyl)-4-{4[(2R,3R,4R)-2,3,4,5-tetrahydroxy-1-(3-thienyl)pentyl]-1-piperazinyl}butyl)-N-methylbenzamide;

N-((2S)-2-(3,4-dichlorophenyl)-4-{4[(2S,3R,4R)-2,3,4,5-tetrahydroxy-1-(2-furyl)pentyl]-1-piperazinyl}-butyl)-N-methylbenzamide;

N-((2S)-2-(3,4-dichlorophenyl)-4-{4[(2R)-2,3-dihydroxy-1-(3-thienyl)propyl]-1-piperazinyl}-butyl)-N-methylbenzamide;

N-((2S)-2-(3,4-dichlorophenyl)-4-{4[(2R,3S,4S)-2,3,4,5-tetrahydroxy-1-(3-thienyl)pentyl]-1-piperazinyl}butyl)-N-methylbenzamide;

N-((2S)-2-(3,4-dichlorophenyl)-4-{4[2S,3R,4R)-2,3,4,5-tetrahydroxyacetyl-1-(3-thienyl)pentyl]-1-piperazinyl}-butyl)-N-methylbenzamide;

N-((2S)-2-(3,4-dichlorophenyl)-4-{4[(2S,3R)-2,3,4-trihydroxy -1-(3-thienyl)butyl]-1-piperazinyl}-butyl)-N-methylbenzamide and N-((2S)-2-(3,4-dichlorophenyl)-4-{2-furyl[(4S)-2-thioxo-1,3-dioxolan-4-yl]methyl}-1-piperazinyl)-butyl]-N-methylbenzamide.

The compounds of Formula I and their acid addition salts may be prepared by reacting a compound of the general Formula II

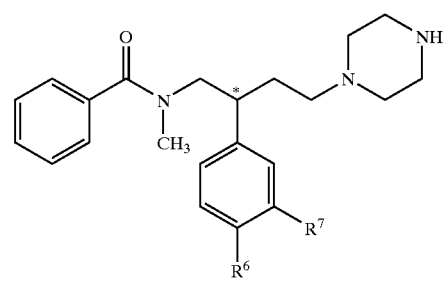

wherein $R^6$ and $R^7$ have the above meanings, with a compound of the general formula III, $$A-B(OH)_2 \qquad III$$

wherein A has the above meaning, and with a compound of the general formula IV,

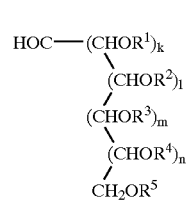

wherein $R^1$, $R^2$, $R^3$, $R^4$, $R^5$, k, l, m und n have the above meanings, and then if desired acylating a resulting compound of Formula I, wherein at least one substituent, selected from $R^1$, $R^2$, $R^3$, $R^4$ and $R^5$, is hydrogen, in the subgroup Z by reacting with a compound of the general formula VIII, $$R^8-COOH \qquad (VIII)$$

wherein $R^8$ has the meaning straight-chain or branched alkyl with 1 to 3 carbon atoms, or then if desired carbonylating or thiocarbonylating respectively a resulting compound of Formula I, wherein at least two substituents, selected from $R^1$, $R^2$, $R^3$, $R^4$ and $R^5$, are hydrogen, in the subgroup Z by reacting with a reactive carbonyl or thiocarbonyl synthesis equivalent, or reacting a resulting compound of Formula I, wherein at least two substituents, selected from $R^1$, $R^2$, $R^3$, $R^4$ and $R^5$, are hydrogen, in the subgroup Z by reacting with a di-lower alkylketone or a $C_{5-6}$-cycloalkylketone to form a 5- or 6-member ring derivative bridged [by] methylene optionally substituted by lower alkyl or $C_{4-5}$-alkylene, and converting a resulting compound of Formula I if desired into its acid addition salt or converting an acid addition salt into a free compound of Formula I.

The reaction can be carried out in known manner under the conditions of a boronic Mannich reaction (cf. e.g. N. A. Petasis et al., Journal of the American Chemical Society 120 (1998) 11798–11799, WO 98/00398 or WO 00/24510). According to this, a compound of Formula II can be reacted in the manner of a one-pot reaction with a boronic acid of Formula III and a carbohydrate of Formula IV which is optionally protected by suitable protective groups in a solvent which is inert under the reaction conditions. Suitable protective groups for carbohydrates are known per se, for example, from J. A. W. McOmie, "Protective Groups in Organic Chemistry", Plenum Press, 1973, or from T. W. Green, P. G. Wuts, "Protective Groups in Organic Synthesis", Wiley and Sons, 1999. Suitable solvents are dipolar-protic organic solvents such as lower alkanols, for example straight-chain or branched $C_{1-4}$-alkanols, preferably ethanol, or mixtures of these aforementioned solvents with water or with dipolar-aprotic solvents such as lower haloalkanes, preferably dichloromethane, are suitable. Suitable reaction temperatures are between room temperature and the boiling point of the solvent or of the solvent mixture. The compounds of Formulae II, III and IV may preferably be combined in succession in this given sequence. Likewise, it is also possible, first to combine a compound of Formula II with a compound of Formula IV and then with a compound of Formula II. The chiral centre bearing the subgroups A and Z newly produced by this coupling reaction in compounds of Formula I is usually formed with a very high degree of diastereo-control as an "anti" product.

The compounds of Formula I which bear at least one free hydroxyl group in the subgroup Z may if desired then also be reacted with compounds of Formula VIII, whereby the free hydroxyl groups of the subgroup Z are acylated. Usually under these circumstances peracylation of the free hydroxyl groups of the subgroup Z takes place. The acids of Formula VIII or their reactive derivatives may be used as acylation agents. In particular acid anhydrides and acid halides are suitable reactive derivatives. The acylation may be carried out in an organic solvent which is inert under the reaction conditions, preferably at temperatures between $-20°$ C. and room temperature. Suitable solvents include in particular aromatic hydrocarbons such as benzene or toluene, cyclic or open-chain di-lower alkyl ethers such as diethyl ether, tetrahydrofuran (=THF) or dioxane, partially halogenated lower hydrocarbons such as dichloromethane or mixtures of these solvents. Where an acid anhydride or an acid halide of the acids of Formula VIII is used as acylation agent, the acylation may expediently take place in the presence of an acid-binding reagent. Suitable acid-binding reagents are non-nucleophilic organic bases soluble in the reaction mixture, such as pyridine, triethylamine or 4-dimethylaminopyridine. Organic bases used in excess can simultaneously also be used as solvents.

The compounds of Formula I which carry at least two free hydroxyl groups in the subgroup Z may if desired, after their preparation described above, also be reacted with a reactive carbonyl- or thiocarbonyl-synthesis equivalent, instead of a reaction with compounds of Formula VIII, whereby the subgroup Z can be carbonylated or thiocarbonylated respectively. The reaction can take place in known manner. For example, a compound of Formula I can be reacted in an organic solvent which is inert under the reaction conditions. Suitable reactive carbonyl synthesis equivalents are for example phosgene or substances which react like phosgene, such as bis-(trichloromethyl)carbonate (=triphosgene), trichloromethyl chloroformate (=diphosgene) or in particular carbonyldiimidazole. Preferably N,N'-thiocarbonyldiimidazole is suitable as reactive thiocarbonyl synthesis equivalent. Expediently an acid-binding reagent may be added to the reaction mixture. Suitable acid-binding reagents are the acid-binding reagents given above for the reaction of compounds of Formula I with compounds of Formula VIII. Suitable reaction temperatures are between about $-20°$ C. and room temperature.

The compounds of Formula I which carry at least two free hydroxyl groups in the subgroup Z may if desired, after their preparation described above, instead of a reaction with compounds of Formula VIII or instead of a reaction with reactive carbonyl or thiocarbonyl synthesis equivalents, also be reacted with a di-lower alkyl ketone or a $C_{5-6}$-cycloalkyl ketone in the subgroup Z, to produce a 5- or 6-member ring derivative bridged [by] methylene optionally substituted by lower alkyl or $C_{4-5}$-alkylene. Preferably acetone is suitable as di-lower alkyl ketone. Preferably cyclopentanone and cyclohexanone are suitable as $C_{5-6}$-cycloalkyl ketones. Where compounds of Formula I are to be prepared in which the substituents contained in the subgroup Z $R^1$, $R^2$, $R^3$, $R^4$ and/or $R^5$ have meanings other than hydrogen, the point of departure is preferably carbohydrate compounds of Formula IV which contain free hydroxyl groups at least in $\alpha$-position to the aldehyde function. It is beneficial to start with compounds of Formula IV wherein $R^1$, $R^2$, $R^3$, $R^4$ and $R^5$ are hydrogen. The free hydroxyl groups may if desired then be acylated, carbonylated, thiocarbonylated or reacted with a suitable ketone in the above manner.

The compounds of Formula II are novel compounds which are advantageously suitable as intermediate products for the preparation of novel active substances, for example for the preparation of the compounds of Formula I, which are antagonistic to tachykinin receptors.

The compounds of Formula II can be prepared by reacting a compound of the general formula V,

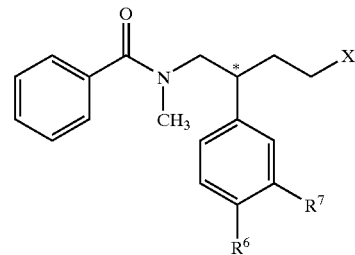

V wherein $R^6$ and $R^7$ have the above meanings and X stands for halogen, in particular for iodine, with a protected piperazine derivative of the general formula VI,

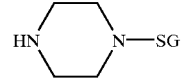

VI wherein SG stands for a cleavable protective group, in particular for tert. butoxycarbonyl, and subsequently cleaving off the protective group SG again in known manner. The reaction can be carried out in an organic solvent which is inert under the reaction conditions, such as an aromatic hydrocarbon, in particular toluene, or in a cyclic or open-chain di-lower alkyl ether, in particular THF, or preferably in a mixture of the aforementioned solvents and in the presence of a base. Suitable bases are non-nucleophilic organic nitrogen bases such as tertiary lower alkylamines, for example triethylamine. Suitable reaction temperatures are between $50°$ and $100°$ C., preferably approximately $70°$ to $90°$ C.

Compounds of Formula V can be prepared by reacting compounds of the general formula VII,

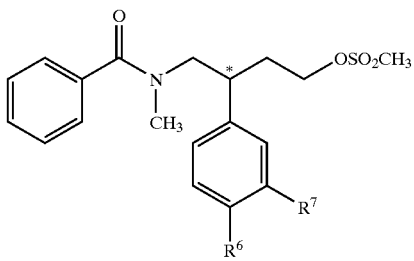

wherein $R^6$ and $R^7$ have the above meanings, in known manner with an alkali metal halide of the general formula MX, wherein M stands for an alkali metal, in particular sodium, and X has the above meaning and stands in particular for iodine. The compounds of Formula VII and their stereoisomeric forms are known per se, for example from EP 0 474 561 A1, and can be prepared according to the processes described in this specification or according to analogous processes.

The compounds of Formulae III, IV and VI are known per se or can be prepared by the person skilled in the art from known compounds in known manner. Compounds of Formula IV which are preferentially used comprise D-xylose, D-lyxose, D-arabinose, D-threose, D-erythrose and D- and L-glyceraldehyde.

The compounds of Formula I may be isolated from the reaction mixture and purified in known manner. Acid addition salts may be converted into the free bases in conventional manner, and these may if desired be converted in known manner into physiologically compatible acid addition salts. Physiologically compatible salts of compounds of Formula I are their conventional salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or trifluoromethanesulfonic acid, or benzenesulfonic acids optionally substituted in the benzene ring by halogen or lower alkyl, such as p-toluenesulfonic acid.

The compounds of Formula I contain in the γ position to the ring nitrogen atom in the 4-position of the piperazine ring an asymmetrical carbon atom, namely the carbon atom *C bearing the phenyl ring substituted by $R^6$ and $R^7$. Due to this asymmetric carbon atom and to the asymmetric carbon atom bearing the subgroups A and Z and optionally also due to the asymmetric carbon atoms contained in the subgroup Z, the compounds of Formula I may exist in several stereoisomeric forms. The present invention covers both the mixtures of optical isomers and the isomerically pure compounds of Formula I. Preferred are compounds of Formula I in which the carbon atom *C bearing the phenyl ring substituted by $R^6$ and $R^7$ is in the S-configuration. If mixtures of optical isomers of the starting compound, for example of the compounds of Formula II or the compounds of Formula IV, are used in the synthesis of the compounds of Formula I, the compounds of Formula I are also obtained in the form of mixtures of optical isomers. Departing from stereochemically uniform forms of the starting compound, stereochemically uniform compounds of Formula I can also be obtained. The stereochemically uniform compounds of Formula I can be obtained from the mixtures of optical isomers in known manner, for example by chromatographic separation on chiral separating materials or by reaction with suitable optically active acids, for example tartaric acid or 10-camphorsulfonic acid, and subsequent separation into their optically active antipodes by fractional crystallization of the diastereomeric salts obtained.

The compounds of Formula I and their acid addition salts have properties which are antagonistic to tachykinin receptors and are therefore suitable for the treatment of pathological conditions in larger mammals, particularly humans, in which tachykinins are involved as transfer agents. The group of compounds according to the invention is distinguished by a particularly beneficial activity profile which is characterized by a high selective affinity to NK-2 receptors. Furthermore, the group of compounds according to the invention is distinguished by good compatibility even over prolonged periods of administration, and by comparatively good oral availability. Due to their activity profile, the compounds of Formula I are suitable in particular for inhibiting processes in which tachykinins, such as neurokinin A, which bind to NK-2 receptors are involved. Due to the action which is advantageously directed at the peripheral region, the compounds of Formula I are suitable in particular for the treatment and/or prophylaxis of functional or inflammatory disorders in the gastrointestinal tract of larger mammals, particularly humans, of both sexes, which involve increased sensitivity to pain and/or impaired stool passage in the colon region. The functional disorders in the gastrointestinal tract which can be treated by the compounds according to the invention include in particular the disorders of the lower intestinal tracts known under the name "irritable bowel syndrome" (=IBS). Typical symptoms for the diagnosis of IBS are described, for example, in W. G. Thompson et al., Gastroenterology International 2 (1989) 92–95 or in W. G. Thompson et al., GUT 45/II (1999) II43–II47, and are generally known among experts by the term "Rome Criteria". The essential symptoms of IBS accordingly include pains in the lower abdomen, which appear to be due to hypersensitivity of the visceral afferent nervous system, and anomalies in bowel movement, such as constipation, diarrhea or alternating constipation and diarrhea. Further inflammatory disorders in the gastrointestinal tract which can be beneficially influenced by the group of compounds according to the invention are for example the inflammatory disorders in the small intestine and large intestine regions usually covered by the term "inflammatory bowel disease" (=IBD), for example ulcerative colitis or Crohn's disease. Due to their mechanism of action, the compounds according to the invention furthermore appear suitable for the treatment of other disorders in which tachykinins and in particular neurokinin A are involved as transfer agents. These disorders include for example neurogenic inflammations, inflammatory joint diseases such as rheumatic arthritis, asthmatic complaints, allergic disorders, disorders of immune regulation, bladder inflammation or also functional dyspepsia.

Description of the Pharmacological Test Methods

The example numbers given for the compounds of Formula I used as test substances in the pharmacological tests given below relate to the following preparation examples.

1. Determination of the Binding Power of the Test Substances to NK-2 Receptors in vitro The affinity of the test substances to human NK-2 receptors was measured in vitro. The ability of the test substances to displace the selective NK-2 receptor antagonist SR 48968 (=saredutant) used as reference ligand from its corresponding bond was determined.

The receptor binding studies were carried out with radioactively marked [$^3$H]-SR 48968 (from Amersham) as ligand. For the binding test, different samples of a membrane preparation of CHO cells (=egg cells of the Chinese hamster, Chinese hamster oocytes), which express the human NK-2 receptor (for preparation, see N. P. Gerard et al., Journal of Biological Chemistry 265/33 (1990) 20455–20462), were incubated for 90 minutes (=min.) with a solution of the marked ligand, with the incubation mixtures containing no test substance or additions of different concentrations of test substance. Then in each case the membrane-bound ligands in the samples were separated from free ligands by filtration. The fraction remaining in the filter was washed several times with buffer solution, before its radioactivity was measured using a liquid scintillation counter. That concentration which effects half-maximum displacement of the bound reference ligand was determined as $IC_{50}$ of the respective test substance. The inhibition constant (Ki value) of the test substance was calculated from the respective $IC_{50}$ value, and was stated as the negative logarithmised value thereof (pKi).

For the compounds of Examples 1 to 39, the affinity to human NK-2 receptors was determined in each case by at least three measurements of the test substances in concentration series of $10^{-6}$ to $10^{-10}$ mol/l. If several measurements were performed, the average thereof was listed each time. All the aforementioned test substances exhibited pKi values of at least 7.0 in this test model. The compounds of Examples 1 to 27 and 39 exhibited pKi values of at least 8.0. The compounds of Examples 1 to 6 and 39 exhibited pKi values of at least 9.0.

2. Determination of the Functional Antagonism of the Test Substances on Isolated Guinea Pig Tissue in vitro The NK-2 receptor-antagonising action of the test substances was determined on isolated gall-bladder preparations from Pirbright-White guinea pigs, held in an oxygen-saturated nutrient solution. To this end, the preparations were fastened on one hand in the nutrient solution to organ holders and on the other hand on a force meter by a thread.

In this test the NK-2 receptors present in the gall-bladder preparations were stimulated with the natural NK-2 receptor agonist neurokinin A (=NKA; 0.1 μmol/l) and the contractions of the preparations caused thereby were measured as contractility in mN (=preliminary value) measured. Then NKA was rinsed out of the preparations with NKA-free solution and the test substances were added in a concentration of $10^{-7}$ mol/l. After two hours' incubation of the preparations with the test substances, the contractions of the preparations then still caused by renewed NKA addition were again measured and the results were given as percentages, relative to the contractions initially measured, caused solely by NKA addition. The concentration of the test substances was increased iteratively in the subsequent experiments as a function of the result in logarithmic whole or half steps, until at least one concentration above or below 50% inhibition of contraction was determined (up to at most $10^{-5}$ mol/l). For each concentration, the average value of inhibition of contraction was calculated from 2 to 4 preparations. In each case, the concentration of half-maximum inhibition ($IC_{50}$) per test substance was calculated as characteristic variable. In each case the logarithmised value of the $IC_{50}$ per test substance is given as $pIC_{50}$ in [mol/l]. In this test model, the test substances set forth in Table 1 below exhibited the $pIC_{50}$ values given below.

TABLE 1

Functional NK-2 antagonism of the test substances on isolated guinea pig tissue

| Example No. | $pIC_{50}$ |
|---|---|
| 1 | 9.8 |
| 7 | 9.6 |
| 9 | 9.3 |
| 13 | 9.4 |
| 14 | 8.7 |
| 17 | 9.7 |

3. Determination of the NK-2-receptor-antagonistic Effectiveness of the Test Substances in vivo The NK-2- and NK-1-antagonistic activities of the test substances were investigated in anaesthetised guinea pigs in each case after intravenous (=i.v.) and oral (=p.o.) administration in vivio. With the present test model it is possible to detect both NK-2-antagonistic effects in three different organ systems (respiratory tracts, colon and circulation) and NK-1-antagonistic effects (rapid drop in blood pressure) in an animal simultaneously.

Pirbright-White guinea pigs of a body weight of 500–700 g were anaesthetised with ketamine/xylazine (67/13 mg/kg subcutaneously, initial dose, further doses administered as required). The animals were provided with an intravenous catheter in order to administer the substance and an intra-arterial catheter to measure the blood pressure. The animals were artificially ventilated via a tracheal cannula and the respiratory pressure was recorded by means of a pressure transducer. A balloon was introduced into the distal colon of the animals for manometric recording of colon motility by means of a pressure transducer. Blood pressure, heart rate, respiratory pressure and colonic pressure were measured continuously for each animal and plotted on a recorder and by means of a digital data-processing system. Neurokinin A (=NKA; 200 pmol/animal) was administered i.v. as a bolus as a test stimulus to stimulate the NK-1- and the NK-2 receptors. An addition of NKA of this type results in a great increase in respiratory pressure (bronchoconstriction) and colonic pressure, and in a biphasic drop in blood pressure. The first phase of hypotension (=phase of maximum hypotension within the first minute after administration of NKA) is mediated via NK-1 receptors, since they can be blocked completely by specific NK-1 receptor antagonists. The second phase of delayed hypotension (=phase of maximum hypotension after 2–5 min.) on the other hand is mediated via NK-2 receptors, since they can be blocked by specific NK-2 receptor antagonists. The doses of the test substances are given as $ED_{50}$ values which each result in a response to the NKA test stimulus which is reduced to 50% of the initial value, as characteristic variables for the individual measurement parameters bronchoconstriction, colonic pressure and change in blood pressure mediated by NK-1 or NK-2.

The antagonistic effects of the test substances were first investigated in cumulative form, the time of the NKA test stimulus being 1 min. after the administration of the respective doses of the test substances had ended. These $ED_{50}$ values obtained from cumulative dose effect curves are plotted in Table 2 (line 1) below. In order additionally to detect the variation over time of the antagonistic effects of the test substances, the action of the NKA test stimulus was determined at different times (1, 30, 60, 90, 120, 150 and 180 min.) after administration of the test substances. The antagonistic effects of the test substances were then determined as "area under the curve" ("AUC") over the investigation period after administration of the test substances (i.v.: 120 min. after administration: p.o.: 180 min. after administration) and the $ED_{50}$ values obtained therefrom were listed in the following Table 2 (lines 2 and 3).

TABLE 2

NK-2-receptor-antagonistic effectiveness of the test substances of Formula I on guinea pigs in vivo

| ED50 | Parameters | Ex. 1 | Ex. 5 | Ex. 13 | Ex. 14 | Ex. 15 |
|---|---|---|---|---|---|---|
| i.v. [µmol/kg] after 1 min. (cumulative) | Colonic pressure | 0.017 | 0.041 | 0.019 | 0.042 | 0.041 |
|  | Respiratory resistance | 0.033 | 0.106 | 0.048 | 0.078 | 0.079 |
|  | Blood pressure | 0.025 | 0.130 | 0.080 | 0.063 | 0.114 |
| i.v. [µmol/kg] AUC over 120 min | Colonic pressure | 0.0009 | 0.014 | 0.018 | — | 0.009 |
|  | Respiratory resistance | 0.008 | 0.008 | 0.023 | — | 0.042 |
|  | Blood pressure | 0.006 | 0.004 | 0.025 | — | 0.047 |
| p.o. [µmol/kg] AUC over 180 min. | Colonic pressure | 0.5 | 3.4 | 1.9 | 3.2 | 4.5 |
|  | Respiratory resistance | 1.8 | 2.7 | 2.0 | 6.7 | 3.2 |
|  | Blood pressure | 2.7 | 7.6 | 24 | 9.4 | 8.6 |

The measured values listed in the foregoing Table 2 show, inter alia, that the substances of Examples 1, 5, 13, 14 and 15 after cumulative administration i.v. (detection of the antagonism 1 min. after the administration of test substance had ended) caused a marked NK-2-receptor-antagonistic activity of colon motility, late drop in blood pressure and respiratory resistance.

The measured values plotted in Table 2 also show that the aforementioned substances, in particular the substance of Example 1, caused more effective inhibition of the NK-2 mechanisms at the colon (colon preference) compared with the inhibition of the bronchoconstrictive or hypotensive NK-2-effects. The compounds according to the invention, in particular the substance of Example 1, are furthermore distinguished by a slow-onset action of long duration.

An NK-1-receptor-antagonistic action could not be observed for any of the investigated test substances at the doses used in vivo.

The compounds of Formula I may be administered in conventional pharmaceutical preparations. The doses to be used may vary individually and will naturally vary according to the type of condition to be treated and the substance used. In general, however, medicinal forms with an active substance content of 0.2 to 200 mg, in particular 1 to 50 mg, active substance per individual dose are suitable for administration to humans and larger mammals. The compounds may be contained according to the invention, together with conventional pharmaceutical auxiliaries and/or carriers, in solid or liquid pharmaceutical preparations. Examples of solid preparations are preparations which can be administered orally, such as tablets, coated tablets, capsules, powders or granules, or alternatively suppositories. These preparations may contain conventional pharmaceutical inorganic and/or organic carriers, such as talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or carriers in known manner. For the production of solid medicament forms, the active substances may for example be mixed with the auxiliaries and/or carriers in conventional manner and may be wet or dry granulated. The granules or powder can be poured directly into capsules or be pressed into tablet cores in conventional manner. These may be coated in known manner if desired.

The following examples are intended to illustrate the invention further, without limiting its scope.

EXAMPLE 1

N-((2S)-2-(3,4-dichlorophenyl)-4-{4-[(2S,3R,4R)-2,3,4,5-tetrahydroxy-1-(3-thienyl)pentyl]-1-piperazinyl}butyl)-N-methylbenzamide.

A) 45.0 g N-[(2S)-2-(3,4-dichlorophenyl)-4-methanesulfonyloxy]-N-methylbenzamide were dissolved in 550 ml acetone under a protective gas atmosphere. 84.6 g NaI was added to this initial solution and the resulting suspension was stirred for 20 hours at room temperature. The solvent was largely evaporated in a vacuum and the remaining residue was taken up in 650 ml methyl tert. butylether (=MTBE) and 500 ml water. After the addition of 120 g $Na_2S_2O_4$, the aqueous phase was separated, and the remaining organic phase was washed four times with 100 ml portions of saturated aqueous common salt solution. The organic phase was dried over sodium sulfate and the solvent was evaporated in a vacuum. Drying the remaining residue in a vacuum yielded 45.9 g N-[(2S)-2-(3,4-dichlorophenyl)-4-iodobutyl]-N-methylbenzamide] as a glassy compound, which was used directly for further reactions without further purification.

B) 15.38 g N-tert. butoxycarbonyl-piperazine was dissolved in 200 ml toluene at room temperature under a protective gas atmosphere and 32 ml triethylamine was added thereto. The resulting solution was heated to 84° C. 45.9 g of the iodide obtained above, dissolved in a mixture of 100 ml THF and 200 ml toluene, was added slowly dropwise to this initial solution. The reaction mixture thus obtained was heated to 80 to 85° C. for 5 hours and then was stirred for another 8 hours at room temperature. The solvent mixture was largely evaporated in a vacuum and the remaining residue was taken up in 600 ml ethyl acetate (=EE). Once the resulting precipitate had been separated out, the organic phase was washed in succession twice with 100 ml water and 100 ml 15%-strength aqueous tartaric acid solution each time. Then 8.0 g NaOH was added to the organic phase and the mixture was washed twice again with 200 ml water each time. Drying of the organic phase over sodium sulfate and evaporation of the solvent in a vacuum yielded 44.9 g tert.butyl-4-[(3S)-4-[benzoyl(methyl)amino]-3-(3,4-dichlorophenyl)butyl]-1-piperazine carboxylate as an oily compound, which was used directly for further reactions without further purification.

C) 44.5 g of the piperazine carboxylate compound obtained above was dissolved in 600 ml methanol at room temperature, 150 ml 6 N HCl was added thereto and the mixture was stirred for 60 hours. Then 500 ml of water was added and the methanol phase was largely evaporated in a vacuum. The remaining aqueous phase was extracted four times with 100 ml portions of EE and four times with 100 ml portions of MTBE. Then a solution of 36.0 g NaOH in 200 ml water was added to the aqueous phase and the now alkaline aqueous phase was extracted twice more with 350 ml portions of EE. The combined organic phases were washed with 100 ml water, dried over sodium sulfate and evaporated in a vacuum. Drying the residue yielded 25.8 g N-[(2S)-2-(3,4-dichlorophenyl)-4-(piperazinyl)-butyl]-N-methylbenzamide as a yellowish, solid oil, which was used directly for further reactions without further purification.

D) 25.0 g of the de-protected piperazine compound obtained above was dissolved in 250 ml ethanol under a protective gas atmosphere at 30° C. Once this initial solution had been heated to 50 to 60° C. first 10.0 g thiophene-3-boronic acid and then 8.93 g D-xylose were added. It was heated to boiling point for 15 hours under reflux cooling and then was stirred for another 8 hours at room temperature. 500 ml water was added and the solvent mixture was largely evaporated in a vacuum. 20 ml 6 N HCl was added to the remaining residue and washing was carried out in succession first once with 200 ml EE, then six times with 100 ml EE each time. The aqueous phase was set to pH 9 to 10 by addition of a corresponding amount of 4 N NaOH and then was extracted with 600 ml dichloromethane. The organic phase was separated, dried over sodium sulfate and finally evaporated in a vacuum. 32.0 g of the title compound was obtained as an amorphous solid, optical rotation $[\alpha]_D^{20}$=−14.8 (c=1 in methanol); $^1$H-NMR (d$_6$-DMSO, 90° C.): 3.81 (d, 1H); 4.15 (dd, 1H); 3.79 (dd, 1H); 3.66 (ddd, 1H); 3.48 (m, 2H); 7.12 (dd, 1H); 7.19 (d, 1H); 7.38 (dd,1H).

EXAMPLE 2

N-((2S)-2-(3,4-dichlorophenyl)-4-{4[(2S)-2,3-dihydroxy-1-(2-furyl)propyl]-1-piperazinyl}-butyl)-N-methylbenzamide 2.08 g N-[(2S)-2-(3,4-dichlorophenyl)-4-(piperazinyl)butyl]-N-methylbenzamide (preparation see above under 1C) was dissolved in 100 ml ethanol and heated to approx. 50° C. 740 mg 2-furanboronic acid and 550 mg of an 80%-strength solution of D-glyceraldehyde in water were added to this initial solution. The resulting solution was heated to boiling at reflux for 10 hours. Then excess solvent was evaporated in a vacuum. Purification of the residue by column chromatography on silica gel (mobile solvent: dichloromethane/EtOH/NH$_4$OH 87/11/2) yielded 2.1 g of the title compound as a beige foam, optical rotation $[\alpha]_D^{20}$=−6.1° (c=1 in methanol); $^1$H-NMR (CDCl$_3$, RT): 3.65 (d, 1H); 4.23 (ddd, 1H); 3.72 (dd, 1H); 3.78 (dd, 1H); 6.27 (d, 1H); 6.37 (1H); 7.42 (1H).

EXAMPLE 3

(2S)-2-(acetyloxy)-3-{4-[(3S)-4-[benzoyl(methyl)amino]-3-(3,4-dichlorophenyl)butyl]-1-piperazinyl}-3-(2-furyl) propylacetate.

1.5 g acetic anhydride was added at room temperature to a solution of 400 mg N-((2S)-2-(3,4-dichlorophenyl)-4-{4-[(2S)-2,3-dihydroxy-1-(2-furanyl)propyl]-1-piperazinyl}-butyl)-N-methylbenzamide (for preparation see Example 2) in 10 ml pyridine. The reaction mixture was stirred for 72 hours and was then poured into a solution of 2.2 g Na$_2$CO$_3$ in 40 ml water. The organic phase was extracted with 60 ml toluene, and the toluene phase was washed three times with 30 ml portions of water and twice with saturated aqueous common salt solution. The combined organic phases were dried over sodium sulfate, and the solvent was evaporated in a vacuum. 463 g of the title compound was obtained as a yellowish foam, $[\alpha]_D^{20}$=+9.6° (c=1 in methanol); $^1$H-NMR (CDCl$_3$, RT): 3.81 (d, 1H); 5.62 (ddd, 1H); 4.58 (dd, 1H); 4.21 (dd, 1H); 1.87 (s, 3H); 2.05 (s, 3H); 6.16 (d, 1H); 6.31 (1H); 7.35 (1H).

EXAMPLE 4

N-[((2S)-2-(3,4)-dichlorophenyl)-4-(4-{2-furyl[(4S)-2-oxo-1,3-dioxolan-4-yl]methyl}-1-piperazinyl)butyl]-N-methylbenzamide 124 mg 4-dimethylaminopyridine (=DMAP) and 410 mg N-carbonyldiimidazole were added to a solution of 576 mg N-((2S)-2-(3,4-dichlorophenyl)-4-{4-[(2S)-2,3-dihydroxy-1-(2-furyl)propyl]-1-piperazinyl}-butyl)-N-methylbenzamide (for preparation see Example 2) in 30 ml dry dichloromethane at room temperature. The reaction mixture was stirred for 15 hours at room temperature and then 3.7 g silica gel was added thereto. The resulting suspension was stirred for another 1 hour, the liquid phase was separated by vacuum filtration and the filtrate was reduced in a vacuum. The remaining residue was taken up in 50 ml EE and the organic phase was washed five times with 10 ml portions of a 50:50 (v/v) mixture of 5%-strength aqueous KH$_2$PO$_4$ solution and 1%-strength aqueous K$_2$HPO$_4$ solution. The organic phase was dried over sodium sulfate and the solvent was then evaporated under vacuum. 460 mg of the title compound was obtained as a white foam, $^1$H-NMR (CDCl$_3$, RT): 3.73 (d, 1H); 5.07 (ddd, 1H); 4.56 (dd, 1H); 4.48 (dd, 1H); 6.3 (d, 1H); 6.378 (1H); 7.41 (1H).

The resulting title compound was dissolved in 4 ml methanol and 0.31 ml of a 1.6 M HCl in isopropanol was added. The dihydrochloride of the title compound was obtained, $[\alpha]_D^{20}$=−28° (c=1 in methanol).

The compounds of Formula I listed in the following Table 3 may also be prepared according to the process described in the foregoing examples or according to processes analogous thereto.

The compounds of Examples 5 to 38 listed in Table 3 were prepared using an automated preparation process. For this, per batch in each case 200 μl of a 0.25 N aqueous stock solution of the corresponding carbohydrate compound of Formula IV was measured in a microreaction vessel and evaporated in a vacuum to largely remove the water. The residue was taken up in 200 μl ethanol. In each case 200 μl of a 0.25 mol/l ethanolic stock solution of racemic or enantiomerically pure (cf. in each case the corresponding particulars in Table 3) N-[2-(3,4-dichlorophenyl)-4-(1-piperazinyl)butyl]-N-methylbenzamide of Formula II and 200 μl of a 0.25 N ethanolic stock solution of the corresponding boronic acid (=dihydroxyborane compound) of Formula III was added to this initial solution. The reaction mixture was first heated to 80° C. for 2 hours and then cooled to room temperature and 1 ml ethanol was added thereto. Then 100 mg basic Amberjet® ion exchange resin was added and the reaction vessel was shaken for 2 hours. The ion exchanger was filtered out, subsequently washed twice with 500 μl portions of ethanol, and the solvent was evaporated to dryness under vacuum. Samples were taken from the residue without further purification in each case for high-performance liquid chromatography (=HPLC) and for automatic mass spectroscopy to determine the purity and to confirm the structure.

TABLE 3

Further compounds of Formula I

| | | | | | Z | | | | | | Configuration | | | | Config. | | MS |
|---|---|---|---|---|---|---|---|---|---|---|---|---|---|---|---|---|---|
| Ex. | A | R¹ | R² | R³ | R⁴ | R⁵ | k | l | m | n | CR¹ | CR² | CR³ | CR⁴ | *C | Salt | [m/z] |
| 5 | 3-thienyl | H | — | — | — | H | 1 | 0 | 0 | 0 | S | — | — | — | S | Base | 576 |
| 6 | 3-furyl | H | — | — | — | H | 1 | 0 | 0 | 0 | S | — | — | — | S | Base | 560 |
| 7 | 3-thienyl | H | H | H | — | H | 1 | 1 | 1 | 0 | S | R | R | — | RS | 2TF | 636 |
| 8 | 3-thienyl | H | — | — | — | H | 1 | 0 | 0 | 0 | S | — | — | — | RS | Base | 576 |
| 9 | 3-thienyl | H | H | H | — | H | 1 | 1 | 1 | 0 | R | R | R | — | RS | 2TF | 636 |
| 10 | 2-furyl | H | H | H | — | H | 1 | 1 | 1 | 0 | S | R | R | — | S | Base | 620 |
| 11 | 3-thienyl | H | — | — | — | H | 1 | 0 | 0 | 0 | R | — | — | — | RS | Base | 576 |
| 12 | 3-thienyl | H | H | H | — | H | 1 | 1 | 1 | 0 | R | S | S | — | S | Base | 636 |
| 13 | 2-furyl | H | H | H | — | H | 1 | 1 | 1 | 0 | S | R | R | — | RS | 2Cl | 620 |
| 14 | 3-thienyl | acetyl | acetyl | acetyl | — | acetyl | 1 | 1 | 1 | 0 | S | R | R | — | S | Base | 804 |
| 15 | 3-thienyl | H | H | — | — | H | 1 | 1 | 0 | 0 | S | R | — | — | S | Base | 606 |
| 16 | 3-thienyl | H | H | — | — | H | 1 | 1 | 0 | 0 | S | S | — | — | RS | Base | 606 |
| 17 | 3-thienyl | H | H | H | — | H | 1 | 1 | 1 | 0 | R | S | R | — | RS | 2TF | 636 |
| 18 | 3-thienyl | H | — | — | — | H | 1 | 0 | 0 | 0 | RS | — | — | — | RS | 2TF | 576 |
| 19 | 2-thienyl | H | H | H | — | H | 1 | 1 | 1 | 0 | R | S | R | — | RS | 2TF | 636 |
| 20 | 3-thienyl | H | H | H | H | H | 1 | 1 | 1 | 1 | R | S | S | S | RS | 2TF | 666 |
| 21 | 3-thienyl | H | H | H | H | H | 1 | 1 | 1 | 1 | R | R | R | R | RS | 2TF | 666 |
| 22 | 2-thienyl | H | — | — | — | H | 1 | 0 | 0 | 0 | RS | — | — | — | RS | 2Cl | 576 |
| 23 | 3-thienyl | H | H | H | H | H | 1 | 1 | 1 | 1 | S | R | R | R | RS | Base | 666 |
| 24 | 2-thienyl | H | H | H | — | H | 1 | 1 | 1 | 0 | S | R | R | — | RS | 2TF | * |
| 25 | phenyl | H | H | H | — | H | 1 | 1 | 1 | 0 | S | R | R | — | RS | Base | 630 |
| 26 | 3-thienyl | — | — | — | — | H | 0 | 0 | 0 | 0 | — | — | — | — | RS | Base | 546 |
| 27 | 3-thienyl | H | H | H | — | H | 1 | 1 | 1 | 0 | R | R | S | — | RS | Base | 636 |
| 28 | 3-thienyl | H | H | — | — | H | 1 | 1 | 0 | 0 | S | R | — | — | RS | Base | 606 |
| 29 | 1-hexenyl | H | H | H | — | H | 1 | 1 | 1 | 0 | R | S | R | — | RS | Base | 636 |
| 30 | 2-furyl | H | H | H | — | H | 1 | 1 | 1 | 0 | S | R | S | — | RS | 2Cl | 620 |
| 31 | 1-(4-phenyl)butenyl | H | H | H | — | H | 1 | 1 | 1 | 0 | R | S | R | — | RS | Base | 684 |
| 32 | 4-methoxyphenyl | H | — | — | — | H | 1 | 0 | 0 | 0 | S | — | — | — | S | Base | 600 |
| 33 | 1-(4-phenyl)butenyl | H | H | H | — | H | 1 | 1 | 1 | 0 | S | R | R | — | RS | Base | 684 |
| 34 | 3-thienyl | H | H | H | H | H | 1 | 1 | 1 | 1 | S | R | S | R | RS | Base | 666 |
| 35 | 3-thienyl | H | H | H | H | H | 1 | 1 | 1 | 1 | S | S | R | R | RS | Base | 666 |
| 36 | 1-(4-phenyl)butenyl | H | H | H | — | H | 1 | 1 | 1 | 0 | R | R | R | — | RS | Base | 684 |
| 37 | 5-indolyl | H | H | H | — | H | 1 | 1 | 1 | 0 | S | R | R | — | RS | 2Cl | ** |
| 38 | 2-naphthyl | H | — | — | — | H | 1 | 0 | 0 | 0 | RS | — | — | — | RS | Bose | 620 |

TF = trifluoroacetate;
MS = mass spectrum
* The compound of Example 24 had the following data in the ¹H-NMR-spectrum (CD₃OD): δ = 3.95 (d); 4.20 (d);
** The compound of Example 37 had the following data in the ¹H-NMR-spectrum (CD₃OD) δ = 4.59 (b); 6.95 (b); 7.19 (b); 7.51 (d); 7.92 (b);

EXAMPLE 39

N-((2S)-2-(3,4-dichlorophenyl)-4-{2-furyl[(4S)-2-thioxo-1,3-dioxolan-4-yl]methyl}-1-piperazinyl)-butyl]-N-methylbenzamide.

240 mg N,N'-thiocarbonyldiimidazole was added to a solution of 303 mg N-((2S)-2-(3,4-dichlorophenyl)-4-{4-[(2S)-2,3-dihydroxy-1-(2-furyl)propyl]-1-piperazinyl}-butyl)-N-methylbenzamide (for preparation see Example 2) in 10 ml dry dichloromethane at room temperature. The reaction mixture was stirred for 20 hours at room temperature and then it was reduced in a water pump vacuum. The remaining residue was taken up in 50 ml EE auf and the organic phase was washed five times with water. The organic phase was dried over sodium sulfate and the solvent was then evaporated in a vacuum (first water pump, then oil pump). Column chromatography of the resulting yellowish foam (stationary phase: silica gel; mobile phase: n-hexane/acetone 1:1) yielded 118 mg of the amorphous title compound, ¹H-NMR (CDCl₃, RT): 3.79 (d, 1H); 5.10 (ddd, 1H); 6.27 (1H); 6.36 (1H).

EXAMPLE I

Capsules Containing N-((2S)-2-(3,4-dichlorophenyl)-4-{4-[(2S,3R,4R)-2,3,4,5-tetrahydroxy-1-(3-thienyl)pentyl]-1-piperazinyl}butyl)-N-methylbenzamide:

Capsules were produced with the following composition per capsule:

| | |
|---|---|
| N-((2S)-2-(3,4-dichlorophenyl)-4-{4-[(2S,3R, 4R)-2,3,4,5-tetrahydroxy-1-(3-thienyl)pentyl]-1-piperazinyl}butyl)-N-methylbenzamide | 20 mg |
| Corn starch | 60 mg |
| Lactose | 300 mg |
| Ethyl acetate | q.s. |

The active substance, the corn starch and the lactose were processed into a homogenous pasty mixture using EE. The paste was ground and the resulting granules were placed on a suitable tray and dried at 45° C. in order to remove the solvent. The dried granules were passed through a crusher and mixed in a mixer with the further following auxiliaries:

| | |
|---|---|
| Talcum | 5 mg |
| Magnesium stearate | 5 mg |
| Corn starch | 9 mg | and then filled into 400 mg capsules (=capsule size 0).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound corresponding to the formula I:

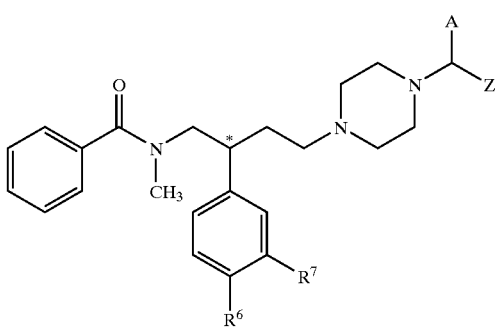

wherein
A is naphthyl, phenyl optionally substituted by hydroxy, mono- or bicyclic heteroaryl selected from the group consisting of thiophene, furan, pyrrole, benzothiophene, benzofuran and indole or $C_{3-6}$-alkenyl optionally substituted by phenyl, Z is a subgroup corresponding to the formula

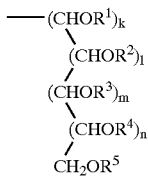

wherein
$R^1$ is hydrogen or lower alkanoyl, or together with another substituent, selected from the group consisting of $R^2$, $R^3$, $R^4$ and $R^5$, may form a 5- or 6-member ring bridged by carbonyl, thiocarbonyl or by methylene optionally substituted by lower alkyl or $C_{4-5}$-alkylene, $R^2$ is hydrogen or lower alkanoyl, or together with another substituent, selected from the group consisting of $R^1$, $R^3$, $R^4$ and $R^5$, may form a 5- or 6-member ring bridged by carbonyl, thiocarbonyl or by methylene optionally substituted by lower alkyl or $C_{4-5}$-alkylene, $R^3$ is hydrogen or lower alkanoyl, or together with another substituent, selected from the group consisting of $R^1$, $R^2$, $R^4$ and $R^5$, may form a 5- or 6-member ring bridged by carbonyl, thiocarbonyl or by methylene optionally substituted by lower alkyl or $C_{4-5}$-alkylene, $R^4$ is hydrogen or lower alkanoyl, or together with another substituent, selected from the group consisting of $R^1$, $R^2$, $R^3$ and $R^5$, may form a 5- or 6-member ring bridged by carbonyl, thiocarbonyl or by methylene optionally substituted by lower alkyl or $C_{4-5}$-alkylene, $R^5$ is hydrogen or lower alkanoyl, or together with another substituent, selected from the group consisting of $R^1$, $R^2$, $R^3$ and $R^4$, may form a 5- or 6-member ring bridged by carbonyl, thiocarbonyl or by methylene optionally substituted by lower alkyl or $C_{4-5}$-alkylene, k is 0 or 1,
l is 0 or 1,
m is 0 or 1 and
n is 0 or 1, $R^6$ is halogen or hydrogen, and
$R^7$ is halogen or hydrogen,
or a physiologically compatible acid addition salt thereof.

2. A compound according to claim 1, wherein A is thiophene or furan.

3. A compound according to claim 1, wherein k is 1 and n is 0.

4. A compound according to claim 1, wherein $R^6$ and $R^7$ each are chlorine.

5. A compound according to claim 1, wherein the asymmetric carbon atom *C is in the S configuration.

6. A compound according to claim 1, wherein said compound is selected from the group consisting of:

N-((2S)-2-(3,4-dichlorophenyl)-4-{4-[(2S,3R,4R)-2,3,4,5-tetrahydroxy-1-(3-thienyl)pentyl]-1-piperazinyl}butyl)-N-methylbenzamide;

N-((2S)-2-(3,4-dichlorophenyl)-4-{4[(2S)-2,3-dihydroxy-1-(2-furyl)propyl]-1-piperazinyl}-butyl)-N-methylbenzamide;

(2S)-2-(acetyloxy)-3-{4-[(3S)-4-[benzoyl(methyl)amino]-3-(3,4-dichlorophenyl)butyl]-1-piperazinyl}-3-(2-furyl)propylacetate;

N-[(2S)-2-(3,4)-dichlorophenyl)-4-(4-{2-furyl[(4S)-2-oxo-1,3-dioxolan-4-yl]methyl}-1-piperazinyl)butyl]-N-methylbenzamide;

N-((2S)2-(3,4-dichlorophenyl)-4-{4[(1S,2R)-2,3-dihydroxy-1-(3-thienyl)propyl]-1-piperazinyl}-butyl)-N-methylbenzamide;

N-((2S)2-(3,4-dichlorophenyl)-4-{4[(2S)-2,3-dihydroxy-1-(3-furyl)propyl]-1-piperazinyl}-butyl)-N-methylbenzamide;

N-((2S)-2-(3,4-dichlorophenyl)-4-{4[(2R,3R,4R)-2,3,4,5-tetrahydroxy-1-(3-thienyl)pentyl]-1-piperazinyl}butyl)-N-methylbenzamide;

N-((2S)-2-(3,4-dichlorophenyl)-4-{4[(2S,3R,4R)-2,3,4,5-tetrahydroxy-1-(2-furyl)pentyl]-1-piperazinyl}-butyl)-N-methylbenzamide;

N-((2S)-2-(3,4-dichlorophenyl)-4-{4[(2R)-2,3-dihydroxy-1-(3-thienyl)propyl]-1-piperazinyl}-butyl)-N-methylbenzamide;

N-((2S)-2-(3,4-dichlorophenyl)-4-{4[(2R,3S,4S)-2,3,4,5-tetrahydroxy-1-(3-thienyl)pentyl]-1-piperazinyl}butyl)-N-methylbenzamide;

N-((2S)-2-(3,4-dichlorophenyl)-4-{4[2S,3R,4R)-2,3,4,5-tetrahydroxyacetyl-1-(3-thienyl)pentyl]-1-piperazinyl}-butyl)-N-methylbenzamide;

N-((2S)-2-(3,4-dichlorophenyl)-4-{4[(2S,3R)-2,3,4-trihydroxy-1-(3-thienyl)butyl]-1-piperazinyl}-butyl)-N-methylbenzamide, and N-((2S)-2-(3,4-dichlorophenyl)-4-{2-furyl[(4S)-2-thioxo-1,3-dioxolan-4-yl]methyl}-1-piperazinyl)-butyl]-N-methylbenzamide.

7. A pharmaceutical composition comprising a pharmacologically effective amount of a compound according to claim 1 and at least one pharmaceutical auxiliary or carrier.

8. A method of inhibiting a functional or inflammatory disorder of a lower intestinal tract of a mammal which involves increased sensitivity to pain or impaired stool passage in the colon region, said method comprising administering to said mammal a pharmaceutically effective amount of a compound according to claim 1.

9. A method according to claim 8, wherein said mammal is a human.

10. A method according to claim 8, wherein said disorder is irritable bowel syndrome.

11. A process for the preparation of a compound corresponding to formula I:

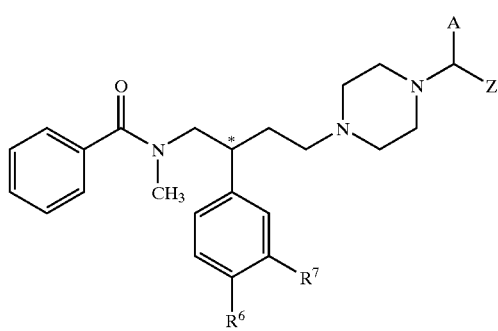

I wherein
A is naphthyl, phenyl optionally substituted by hydroxy, mono- or bicyclic heteroaryl selected from the group consisting of thiophene, furan, pyrrole, benzothiophene, benzofuran and indole or $C_{3-6}$-alkenyl optionally substituted by phenyl, Z is a subgroup corresponding to the formula

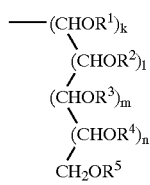

wherein
$R^1$ is hydrogen or lower alkanoyl, or together with another substituent, selected from the group consisting of $R^2$, $R^3$, $R^4$ and $R^5$, may form a 5- or 6-member ring bridged by carbonyl, thiocarbonyl or by methylene optionally substituted by lower alkyl or $C_{4-5}$-alkylene, $R^2$ is hydrogen or lower alkanoyl, or together with another substituent, selected from the group consisting of $R^1$, $R^3$, $R^4$ and $R^5$, may form a 5- or 6-member ring bridged by carbonyl, thiocarbonyl or by methylene optionally substituted by lower alkyl or $C_{4-5}$-alkylene, $R^3$ is hydrogen or lower alkanoyl, or together with another substituent, selected from the group consisting of $R^1$, $R^2$, $R^4$ and $R^5$, may form a 5- or 6-member ring bridged by carbonyl, thiocarbonyl or by methylene optionally substituted by lower alkyl or $C_{4-5}$-alkylene, $R^4$ is hydrogen or lower alkanoyl, or together with another substituent, selected from the group consisting of $R^1$, $R^2$, $R^3$ and $R^5$, may form a 5- or 6-member ring bridged by carbonyl, thiocarbonyl or by methylene optionally substituted by lower alkyl or $C_{4-5}$-alkylene, $R^5$ is hydrogen or lower alkanoyl, or together with another substituent, selected from the group consisting of $R^1$, $R^2$, $R^3$ and $R^4$, may form a 5- or 6-member ring bridged by carbonyl, thiocarbonyl or by methylene optionally substituted by lower alkyl or $C_{4-5}$-alkylene, k is 0 or 1,
l is 0 or 1,
m is 0 or 1 and
n is 0 or 1,
$R^6$ is halogen or hydrogen, and
$R^7$ is halogen or hydrogen,
or a physiologically compatible acid addition salt thereof, said process comprising reacting a compound of formula II:

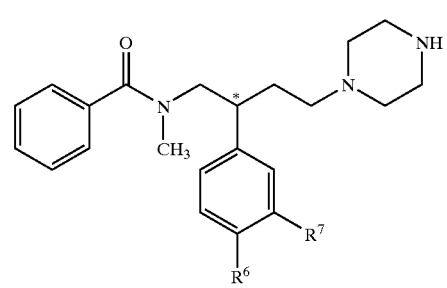

II wherein $R^6$ and $R^7$ have the above meanings,
with a compound of formula III:

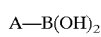

III wherein A has the above meaning,
and with a compound of formula IV:

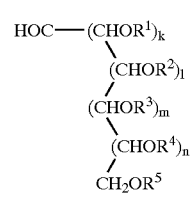

IV wherein $R^1$, $R^2$, $R^3$, $R^4$, $R^5$, k, l, m und n have the above meanings, and optionally acylating a resulting compound of Formula I, wherein at least one substituent selected from $R^1$, $R^2$, $R^3$, $R^4$ and $R^5$ is hydrogen, in the subgroup Z by reacting with a compound corresponding to formula VIII:

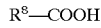

(VIII)

wherein $R^8$ is a straight-chain or branched alkyl with 1 to 3 carbon atoms, or optionally carbonylating or thiocarbonylating a resulting compound of Formula I, wherein at least two substituents selected from $R^1$, $R^2$, $R^3$, $R^4$ and $R^5$ are hydrogen, in the subgroup Z by reacting the compound of formula I with a reactive carbonyl- or thiocarbonyl synthesis equivalent, or optionally converting a resulting compound of Formula I, wherein at least two substituents, selected from $R^1$, $R^2$, $R^3$, $R^4$ and $R^5$ are hydrogen, to a 5- or 6-member ring derivative bridged by methylene and optionally substituted by lower alkyl or $C_{4-5}$-alkylene by reacting the compound of Formula I in the subgroup Z with a di-lower alkylketone or a $C_{5-6}$-cycloalkylketone, and optionally converting compound of Formula I into a corresponding acid addition salt, or optionally converting an acid addition salt into a free compound of Formula I.

12. A compound corresponding to formula II:

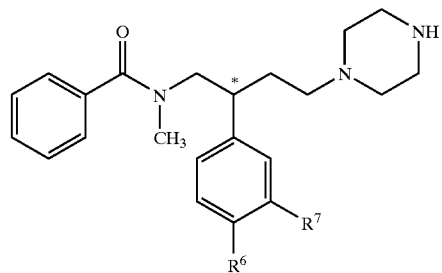

wherein $R^6$ is halogen or hydrogen, and $R^7$ is halogen or hydrogen.

* * * * *

UNITED STATES PATENT AND TRADEMARK OFFICE
Certificate

Patent No. 6,770,649 B2

Patented: August 3, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Daniel Jasserand, Hannover (DE); Ulf Preuschoff, Lehrte/Ahlten (DE); Jochen Antel, Bad Muender (DE); Samuel David, Hannover (DE); Holger Sann, Hannover (DE); Reinhard Brueckner, Hannover (DE); Dania Reiche, Adelheidsdorf (DE); Christian Eeckhout, Lindwedel (DE); Alan P. Kaplan, New York, NY (US); Belew Mekonnen, Gilbertsville, NY (US); Binaya Kansakar, De Built, NY (US).

Signed and Sealed this Twenty-Fourth Day of April 2007.

WILLIAM R. DIXON, JR.
Technology Center 1600

UNITED STATES PATENT AND TRADEMARK OFFICE
Certificate

Patent No. 6,770,649 B2                                                                 Patented: August 3, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Daniel Jasserand, Hannover (DE); Ulf Preuschoff, Lehrte/Ahlten (DE); Jochen Antel, Bad Muender (DE); Samuel David, Hannover (DE); Holger Sann, Hannover (DE); Reinhard Brueckner, Hannover (DE); Dania Reiche, Adelheidsdorf (DE); Christian Eeckhout, Lindwedel (DE); Alan P. Kaplan, New York, NY (US); Belew Mekonnen, Gilbertsville, NY (US); and Binaya Kansakar, De Built (NL).

Signed and Sealed this Tenth Day of July 2007.

WILLIAM R. DIXON, JR.
Technology Center 1600